United States Patent [19]

Arcari et al.

[11] 4,141,899
[45] Feb. 27, 1979

[54] 4,5,6,7-TETRAHYDROIMIDAZO-[4,5-C]-PYRIDINE DERIVATIVES

[75] Inventors: Giuliana Arcari; Luigi Bernardi; Giovanni Falconi; Fulvio Luini; Giorgio Palamidessi; Ugo Scarponi, all of Milan, Italy

[73] Assignee: Societa' Farmaceutici Italia S.p.A., Milan, Italy

[21] Appl. No.: 838,844

[22] Filed: Oct. 3, 1977

Related U.S. Application Data

[63] Continuation-in-part of Ser. No. 756,290, Jan. 3, 1977, abandoned.

[30] Foreign Application Priority Data

Jan. 7, 1976 [GB] United Kingdom ............... 00573/76
Jun. 29, 1976 [GB] United Kingdom ............... 27071/76

[51] Int. Cl.² .................................... C07D 471/04
[52] U.S. Cl. ................................. 546/118; 424/256
[58] Field of Search ................. 260/295 F, 294.8 C

[56] References Cited

U.S. PATENT DOCUMENTS

| 3,960,876 | 6/1976 | Curran | 260/294.8 C |
|---|---|---|---|
| 4,085,215 | 3/1978 | Curran et al. | 424/258 |
| 4,092,320 | 5/1978 | Curran et al. | 260/294.8 C |

Primary Examiner—Alan L. Rotman
Attorney, Agent, or Firm—Stevens, Davis, Miller & Mosher

[57] ABSTRACT

New 4,5,6,7-tetrahydroimidazo-[4,5-c]-pyridine derivatives are disclosed, and more particularly derivatives of Formula I

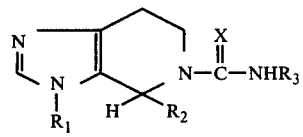

where
$R_1$ is hydrogen or an alkyl having from 1 to 4 carbon atoms;
$R_2$ is hydrogen, an alkyl having from 1 to 4 carbon atoms, a cycloalkyl having from 3 to 6 carbon atoms, phenyl or a heterocycle;
$R_3$ is hydrogen, a saturated or unsaturated straight or branched alkyl having from 1 to 6 carbon atoms, a cycloalkyl having from 3 to 6 carbon atoms, benzoyl or phenyl; and
X is O, S or $NR_4$ where $R_4$ is hydrogen, an alkyl having from 1 to 4 carbon atoms, cyano, amino, nitro or acylamino;

or pharmaceutically acceptable acid addition salts thereof. Also disclosed is a process of preparing these compounds which comprises condensing an appropriate 4,5,6,7-tetrahydroimidazo-[4,5-c]-pyridine with an appropriate alkyl isocyanate, alkyl isothiocyanate or substituted S-methyl thiourea, preferably in a solvent such as ethanol, acetonitrile or dioxane, usually under reflux for from 4 to 12 hours. The products can be isolated by crystallization as free bases or as salts of pharmaceutically acceptable acids. The new compounds have proved to be well tolerated and to inhibit both the number of experimental ulcers and the gastric secretion in experimental animals. Thus, they should prove useful in the therapy of gastric and duodenal ulcers in man.

38 Claims, No Drawings

4,5,6,7-TETRAHYDROIMIDAZO-[4,5-c]-PYRIDINE DERIVATIVES

This application is a continuation-in-part of our prior application Ser. No. 756,290, filed Jan. 3, 1977, now abandoned.

This invention relates to new 4,5,6,7-tetrahydroimidazo-[4,5-c]-pyridine derivatives.

This invention provides new derivatives of the formula I:

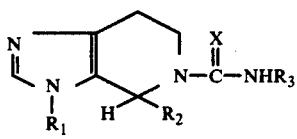

where
$R_1$ is hydrogen or an alkyl having from 1 to 4 carbon atoms;
$R_2$ is hydrogen, an alkyl having from 1 to 4 carbon atoms, a cycloalkyl having from 3 to 6 carbon atoms, phenyl or a heterocycle;
$R_3$ is hydrogen, a saturated or unsaturated straight or branched alkyl having from 1 to 6 carbon atoms, a cycloalkyl having from 3 to 6 carbon atoms, benzoyl or phenyl; and
X is O, S or $NR_4$ where $R_4$ is hydrogen, an alkyl having from 1 to 4 carbon atoms, cyano, amino, nitro or acylamino;
or a pharmaceutically acceptable acid addition salt thereof.

This invention includes a process of preparing these compounds which comprises condensing an appropriate 4,5,6,7-tetrahydroimidazo-[4,5-c]-pyridine with an appropriate alkyl isocyanate, alkyl isothiocyanate or substituted S-methyl thiourea, preferably in a solvent such as ethanol, acetonitrile or dioxane, usually under reflux for from 4 to 12 hours. The products can be isolated by crystallization as free bases or as salts of pharmaceutically acceptable acids.

The new compounds of this invention have proved to be well tolerated and to inhibit both the number of experimental ulcers and the gastric secretion in experimental animals. Thus, they should prove useful in the therapy of gastric and duodenal ulcers in man.

The activity of these compounds has been assessed in rats in anti-ulcer and anti-secretory tests. Methiamide, which is well known for its antisecretory activity (Wyllie et al.: Gut, 1973, 14, 424), and is considered one of the most active substances in this field (S. Dai et al., Eur. J. Pharm., 1975, 33, 277), was adopted as the reference standard.

1. Inhibition of restraint ulcer in rats (Bonfils et al., Thérapie, 1960, 15, 1096). Six Sprague-Dawley male rats (100–200 g) fasted for 24 hours were used for each group.

A square flexible small-mesh wire netting was used for immobilization. After 4 hours immobilization the rats were sacrificed, their stomachs were removed, and lesions counted under a dissecting microscope.

The obtained results were reported in Table I, wherein the values are given as $ED_{50}$.

The compounds were administered subcutaneously (s.c.) immediately before the immobilization or orally (os) one hour before.

2. Inhibition of gastric secretion in rats (Shay, Gastroenterology, 1945, 43, 5). Gastric antisecretory activity was evaluated in rats by the pylorus ligature technique.

Six Sprague-Dawley male rats (110–130 g) were used for each group. Twenty-four hours before the test, the rats were deprived of food but their water supply was maintained.

On the day of the operation, the pylorus was ligated under light ether anaesthesia. Four hours after the ligature, the rats were sacrificed, the stomach secretion was collected and centrifuged at 3500 r.p.m. for 10 minutes, and the volume, less sediment, was determined. The amount of the free hydrochloric acid in the gastric juice was determined by titration against 0.01N sodium hydroxide, using Topfer's Indicator.

Each compound was injected subcutaneously at the time of ligature.

3. Anticholinergic activity in rats. Considering that many anti-ulcer agents display as atropine a remarkable anti-cholinergic activity, some derivatives have been also orally assessed for their antagonism against chromodacryorhea induced by carbacholine in rats (Winburg M. et al.: J. Pharm. Exp. Therap., 1949, 95, 53). From 3 to 5 Sprague-Dawley male rats, 250 g body weight, have been employed for each group.

The Table shows the results obtained expressed as $ED_{50}$. The compound reference numbers are explained in the Examples below.

TABLE

| 386 | $ED_{50}$ (mg/kg) in rats | | | | |
|---|---|---|---|---|---|
| | Antiulcer | | Anti-secretory s.c. | anti-cholinergic p.o. (B) | B/A |
| | s.c. | p.o (A) | | | |
| 1068 | 0.6 | 2.4 | >50 | >100 | >40 |
| 1087 | 0.9 | 3.1 | 6 | 2 | 0.6 |
| 1116 | >10 | >34 | 23 | — | — |
| 1184 | 0.64 | 11 | 22 | 10 | 0.3 |
| 1286 | 0.85 | 8.5 | 34 | >50 | >5.8 |
| 1293 | 6 | 25 | 8 | — | — |
| 1359 | 5 | 1.8 | 40 | 45.5 | 25 |
| 1360 | >10 | 5.6 | 19 | 76 | 13 |
| 1361 | 10 | 25 | 50 | — | — |
| 1367 | 3.3 | 6 | >50 | >100 | >18 |
| 1399 | 3.5 | 4 | >100 | >25 | |
| 1316 | 0.75 | 6.6 | 50 | 70 | 10 |
| 1348 | 0.1 | 0.55 | 18 | 7.8 | 14 |
| 1350 | 6.5 | 5.6 | >50 | >100 | >18 |
| 1365 | 2 | 3.8 | 50 | 21 | 5.5 |
| 1366 | 0.75 | 3.8 | 17 | 10 | 2.6 |
| 1400 | 10 | 18 | 50 | >100 | >5.5 |
| 1404 | 10 | 34 | >50 | — | — |
| 1467 | 7 | 50 | >50 | — | — |
| 1448 | >10 | 22 | >50 | >100 | >4 |
| 1450 | >10 | 34 | >50 | — | — |
| Methiamide | 14 | 64 | 60 | 85 | 1.3 |
| Atropine | 0.02 | 0.4 | 0.1 | 0.8 | 2 |

As appears from the Table, showing the ratios between the $ED_{50}$'s for the oral anti-cholinergic and anti-ulcer activities, some derivatives display an anti-ulcer activity at doses up to 40 times lower than those active as anti-cholinergic.

For both atropine and methiamide such a ratio is about 2.

In the therapeutic field, the products of the present invention may be administered by the oral or the parenteral route. The therapeutic compositions normally employed include one or more compounds of the present invention with a conventional quantity of a solid or a liquid vehicle. The compositions may be prepared as tablets, powders, pills or other forms pharmaceutically suitable for oral or parenteral administration. Liquid diluents duly sterilized are employed for the parenteral administration. Conventional excipients may be employed, among which the most common are starch, lactose, talc, magnesium stearate, and the like.

This invention is illustrated by the following Examples in which all temperatures are in degrees Celsius (C).

EXAMPLE 1

5-(N-methyl-thiocarbamoyl)-4,5,6,7-tetrahydroimidazo-[4,5-c]-pyridine (386/1068)

A solution of 1 g of 4,5,6,7-tetrahydro-imidazo-[4,5-c]-pyridine (Farmaco, *Ed. Sci.,* 1967, 22, 821) and 0.65 g of methyl isothiocyanate in 20 ml of ethanol are refluxed for 8 h. The solution is cooled and filtered: 1.15 g of 5-(N-methyl-thiocarbamoyl)-4,5,6,7-tetrahydroimidazo-[4,5-c]-pyridine, m.p. 228°, are collected.

EXAMPLE 2

5-(N-ethyl-thiocarbamoyl)-4,5,6,7-tetrahydro-imidazo-[4,5-c]-pyridine (386/1293)

A solution of 1.85 g of 4,5,6,7-tetrahydro-imidazo-[4,5-c]-pyridine and 2 g of ethyl isothiocyanate in 15 ml of acetonitrile are refluxed for 7 h. The solution is cooled and filtered: 2.5 g of 5-[N-ethyl-thiocarbamoyl]-4,5,6,7-tetrahydro-imidazo-[4,5-c]-pyridine, m.p. 185°, are collected.

EXAMPLE 3

5-(N-n-propyl-thiocarbamoyl)-4,5,6,7-tetrahydro-imidazo-[4,5-c]-pyridine (386/1361)

Operating as in Example 1, but employing propyl isothiocyanate, the product is obtained in 81% yield, m.p. 151°.

EXAMPLE 4

5-(N-isopropyl-thiocarbamoyl)-4,5,6,7-tetrahydro-imidazo-[4,5-c]-pyridine (386/1087)

A solution of 2 g of 4,5,6,7-tetrahydro-imidazo-[4,5-c]-pyridine hydrochloride and 2.5 g of isopropyl isothiocyanate in 20 ml of acetonitrile and 5 ml of ethanol is refluxed 8 h. Evaporation of the solvent leaves a residue that is treated with one equivalent of ethanolic hydrogen chloride. Evaporation of the solvent leaves a residue which is crystallized from acetone to give 2.5 g of 5-(N-isopropyl-thiocarbamoyl)-4,5,6,7-tetrahydro-imidazo-[4,5-c]-pyridine hydrochloride, m.p. 170°.

EXAMPLE 5

5-(N-n-butyl-thiocarbamoyl)-4,5,6,7-tetrahydro-imidazo-[4,5-c]-pyridine (386/1331)

Operating as in Example 1, but employing butyl isothiocyanate the product is obtained in 75% yield, m.p. 130°.

EXAMPLE 6

5-(N-cyclohexyl-thiocarbamoyl)-4,5,6,7-tetrahydro-imidazo-[4,5-c]-pyridine (386/1294)

Operating as in Example 2, but employing cyclohexyl isothiocyanate the product, m.p. 183°, is obtained in 82% yield.

EXAMPLE 7

4-Ethyl-5-(N-methyl-thiocarbamoyl)-4,5,6,6-tetrahydro-imidazo-[4,5-c]-pyridine (386/1214)

A solution of 2.9 g of 4-ethyl-4,5,6,7-tetrahydro-imidazo-[4,5-c]-pyridine (Farmaco, *Ed. Sci.* 1967, 22, 821) and 3 g of methyl isothiocyanate in 32 ml of acetonitrile and 8 ml of ethanol is refluxed for 8 h. The solution is evaporated in vacuo, and the residue crystallized from diethyl ether to give 3 g of 4-ethyl-5-(N-methyl-thiocarbamoyl)-4,5,6,7-tetrahydro-imidazo-[4,5-c]-pyridine, m.p. 230°.

EXAMPLE 8

5-(N-allyl-thiocarbamoyl)-4,5,6,7-tetrahydro-imidazo-[4,5-c]-pyridine (386/1185)

Operating as in Example 2, but employing allylisothiocyanate, the product, m.p. 172°, is obtained in 71% yield.

EXAMPLE 9

4-Ethyl-5-(N-isopropyl-thiocarbamoyl)-4,5,6,7-tetrahydro-imidazo-[4,5-c]-pyridine (386/1184)

Operating as in Example 7, but employing isopropyl isothiocyanate, the product, m.p. 215°, is obtained in 79% yield.

EXAMPLE 10

4-Ethyl-5-(N-allyl-thiocarbamoyl)-4,5,6,7-tetrahydro-imidazo-[4,5-c]-pyridine (386/1216)

Operating as in Example 7, but employing allyl isothiocyanate, the product, m.p. 205°, is obtained in 70% yield.

EXAMPLE 11

4-Ethyl-5-(N-butyl-thiocarbamoyl)-4,5,6,7-tetrahydro-imidazo-[4,5-c]-pyridine (386/1215)

Operating as in Example 7, but employing butyl isothiocyanate, the product, m.p. 180°, is obtained in 75% yield.

EXAMPLE 12

4-Phenyl-5-(N-methyl-thiocarbamoyl)-4,5,6,7-tetrahydro-imidazo-[4,5-c]-pyridine (386/1254)

A solution of 3.5 g of 4-phenyl-4,5,6,7-tetrahydro-imidazo-[4,5-c]-pyridine (Farmaco, *Ed. Sci.,* 1967, 22, 821) and 3.5 g of methyl isothiocyanate in 55 ml of dioxane is refluxed for 4 h. The solution is cooled and filtered: 3.6 g of 4-phenyl-5-(N-methyl-thiocarbamoyl)-4,5,6,7-tetrahydroimidazo-[4,5-c]-pyridine, m.p. 228°, are collected.

EXAMPLE 13

4-Phenyl-5-(N-isopropyl-thiocarbamoyl)-4,5,6,7-tetrahydro-imidazo-[4,5-c]-pyridine (386/1253)

Operating as in Example 12, but employing isopropyl isothiocyanate, the product, m.p. 198°, is obtained in 80% yield.

EXAMPLE 14

4-iso-propyl-5-(N-methyl-thiocarbamoyl)-4,5,6,7-tetrahydro-imidazo-[4,5-c]-pyridine (386/1257)

To a solution of 20 g of histamine dihydrochloride in 54 ml of water and 440 ml of methanol, 19.6 g of sodium hydroxide dissolved in 54 ml of water and 25 ml of isobutyraldehyde are added and the solution refluxed for 24 h. The solution is then acidified with 200 ml of conc. hydrochloric acid and evaporated in vacuo. The residue is taken up in methanol. The methanolic extract is evaporated in vacuo to give 23 g of 4-isopropyl-4,5,6,7-tetrahydro-imidazo-[4,5-c]-pyridine dihydrochloride, m.p. 238°, from which the free base, m.p. 112°, is obtained by ion-exchange on Amberlite (Trade Mark) IRA 410. A solution of 1.3 g of the base in 10 ml of dioxane is treated with 1.3 g of methyl isothiocyanate and refluxed for 4 h. The solution is cooled and filtered; 1.4 g of 4-isopropyl-5-(N-methyl-thiocarbamoyl)-4,5,6,7-tetrahydro-imidazo-[4,5-c]-pyridine, m.p. 240°, are collected.

EXAMPLE 15

4-iso-propyl-5-(N-isopropyl-thiocarbamoyl)-4,5,6,7-tetrahydro-imidazo-[4,5-c]-pyridine (386/1258)

Operating as in Example 14, but employing isopropyl isothiocyanate, the product, m.p. 203°, is obtained in 80% yield.

EXAMPLE 16

3-Methyl-5-(N-methyl-thiocarbamoyl)-4,5,6,7-tetrahydro-imidazo-[4,5-c]-pyridine (386/1276)

A solution of 1 g of 3-methyl-4,5,6,7-tetrahydro-imidazo-[4,5-c]-pyridine and 1 g of methyl isothiocyanate in 10 ml of acetonitrile is refluxed for 4 h. The solution is cooled and filtered: 0.9 g of 3-methyl-5-(N-methyl-thiocarbamoyl)-4,5,6,7-tetrahydro-imidazo-[4,5-c]-pyridine, m.p. 235°, are collected.

EXAMPLE 17

3-Methyl-5-(N-isopropyl-thiocarbamoyl-4,5,6,7-tetrahydro-imidazo-[4,5-c]-pyridine (386/1286)

Operating as in Example 16, but employing isopropyl isothiocyanate, the product, m.p. 205°, is obtained in 66% yield.

EXAMPLE 18

5-(N-Phenyl-thiocarbamoyl)-4,5,6,7-tetrahydro-imidazo-[4,5-c]-pyridine (386/1116)

Operating as in Example 2, but employing phenyl isothiocyanate, the product, m.p. 205°, is obtained in 82% yield.

EXAMPLE 19

5-(N-cyano-N'-methyl-guanyl)-4,5,6,7-tetrahydro-imidazo-[4,5-c]-pyridine (386/1347)

A solution of 1.23 g of 4,5,6,7-tetrahydro-imidazo-[4,5-c]-pyridine and 1.29 g of N,S-dimethyl-N'-cyano-isothiourea

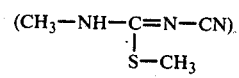

in 15 ml of acetonitrile is refluxed for 21 h. After evaporation to dryness, chromatography on silica gel (ethyl acetate-ethanol as eluant) of the residue gives 630 mg of the pure title compound, m.p. 240°.

EXAMPLE 20

5-Guanyl-4,5,6,7-tetrahydro-imidazo-[4,5-c]-pyridine (386/1289)

A solution of 1.23 g of 4,5,6,7-tetrahydro-imidazo-[4,5-c]-pyridine and 0.9 g of S-methyl-isothiourea in 15 ml of acetonitrile is refluxed for 8 h. After evaporation to dryness, the residue is treated with one equivalent of ethanolic hydrogen chloride. After cooling, 1.4 g of 5-guanyl-4,5,6,7-tetrahydro-imidazo-[4,5-c]-pyridine monohydrochloride, m.p. 310°, are collected.

EXAMPLE 21

4-Ethyl-5-guanyl-4,5,6,7-tetrahydro-imidazo-[4,5-c]-pyridine (386/1284)

Operating as in Example 20, 15. g of 4-ethyl-5-guanyl-4,5,6,7-tetrahydro-imidazo-[4,5-c]-pyridine monohydrochloride, m.p. 300° (dec.), are obtained from 1.51 g of 4-ethyl-4,5,6,7-tetrahydro-imidazo-[4,5-c]-pyridine.

EXAMPLE 22

4-Ethyl-5-(N-ethyl-guanyl)-4,5,6,7-tetrahydro-imidazo-[4,5-c]-pyridine (386/1336)

A solution of 1.5 g of 4-ethyl-4,5,6,7-tetrahydro-imidazo-[4,5-c]-pyridine and 1.18 g of N-ethyl-S-methyl-isothiourea in 15 ml of acetonitrile is refluxed for 8 h. After evaporation to dryness the residue is treated with one equivalent of ethanolic hydrogen bromide. After cooling, 1.5 g of 4-ethyl-5-(N-ethyl-guanyl)-4,5,6,7-tetrahydro-imidazo-[4,5-c]-pyridine monohydrobromide, m.p. 275°, are collected.

EXAMPLE 23

4-Ethyl-5-(N-isopropyl-guanyl)-4,5,6,7-tetrahydro-imidazo-[4,5-c]-pyridine (386/1337)

Operating as in Example 22, but employing N-isopropyl-S-methyl-isothiourea, 1.6 g of 4-ethyl-5-(N-isopropyl-guanyl)-4,5,6,7-tetrahydro-imidazo-[4,5-c]-pyridine monohydrobromide (m.p. 280° (dec.)) are obtained.

EXAMPLE 24

5-(N-ethyl-guanyl)-4,5,6,7-tetrahydro-imidazo-[4,5-c]-pyridine

Operating as in Example 22, the monohydrobromide of the title compound is obtained in 50% yield from 4,5,6,7-tetrahydroimidazo-[4,5-c]-pyridine.

EXAMPLE 25

5-(N-isopropyl-guanyl)-4,5,6,7-tetrahydro-imidazo-[4,5-c]-pyridine

Operating as in Example 23, the monohydrobromide of the title compound is obtained in 55% yield from 4,5,6,7-tetrahydroimidazo-[4,5-c]-pyridine.

EXAMPLE 26

4-Phenyl-5-(N-methyl-carbamoyl)-4,5,6,7-tetrahydro-imidazo-[4,5-c]-pyridine (386/1261)

A solution of 3 g of 4-phenyl-4,5,6,7-tetrahydro-imidazo-[4,5-c]-pyridine and 3.42 g of methyl isocyanate in 40 ml of dry dioxane is refluxed for 1.5 h. Evaporation to dryness gives a solid (4.72 g) that is washed with some ethyl acetate, dissolved in 60 ml of methanol and treated with 15 ml of 2N sodium hydroxide for 2 h at room temperature. After neutralization, the solution is extracted with chloroform. Evaporation of the solvent leaves a residue that is taken up in ethyl acetate to give 2.5 g of the title compound, m.p. 180°.

EXAMPLE 27

4-Phenyl-5-(N-isopropyl-carbamoyl)-4,5,6,7-tetrahydro-imidazo-[4,5-c]-pyridine (386/1351)

Operating as in Example 26, but employing isopropyl isocyanate, 3.11 g of the title compound, m.p. 245°, are obtained.

EXAMPLE 28

4-Ethyl-5-(N-methyl-carbamoyl)-4,5,6,7-tetrahydro-imidazo-[4,5-c]-pyridine (386/1295)

A solution of 1.51 g of 4-ethyl-4,5,6,7-tetrahydro-imidazo-[4,5-c]-pyridine and 2.28 g of methyl isocyanate in 20 ml of dry dioxane is refluxed for 1.5 h. The solution is cooled and filtered. The solid collected is dissolved in 30 ml of methanol and treated with 7 ml of 2N sodium hydroxide for 2 h at room temperature. After neutralization the solution is extracted with chloroform. Evaporation of the solvent leaves a residue that is taken up in ethyl acetate. 1.05 g of the title compound, m.p. 240°, are collected.

EXAMPLE 29

4-Ethyl-5-(N-isopropyl-carbamoyl)-4,5,6,7-tetrahydro-imidazo-[4,5-c]-pyridine (386/1316)

Operating as in Example 28, employing isopropyl isocyanate, the title compound, m.p. 170°, is obtained in 70% yield.

EXAMPLE 30

5-(N-methyl-carbamoyl)-4,5,6,7-tetrahydro-imidazo-[4,5-c]-pyridine (386/1350)

Operating as in Example 28, 1.8 g of the title compound, m.p. 213°, are obtained from 2.46 g of 4,5,6,7-tetrahydro-imidazo-[4,5-c]-pyridine.

EXAMPLE 31

5-(N-isopropyl-carbamoyl)-4,5,6,7-tetrahydro-imidazo-[4,5-c]-pyridine (386/1348)

A solution of 2.46 g of 4,5,6,7-tetrahydro-imidazo-[4,5-c]-pyridine and 6.8 g of isopropyl isocyanate in 50 ml of dry dioxane is refluxed for 2 h. After evaporation to dryness, the residue is dissolved in 25 ml of methanol and treated with 12.5 ml of 2N sodium hydroxide for 2 h at room temperature. After neutralization, the solution is extracted with chloroform. Evaporation of the solvent leaves a residue (2.21 g, oil) that is treated with one equivalent of hydrogen chloride in isopropanol. After cooling, 1.7 g of 5-(N-isopropyl-carbamoyl)-4,5,6,7-tetrahydro-imidazo-[4,5-c]-pyridine hydrochloride, m.p. 190°, are collected.

EXAMPLE 32

5-(N-cyclopropyl-carbamoyl)-4,5,6,7-tetrahydro-imidazo-[4,5-c]-pyridine (386/1365)

A solution of 3.69 g of 4,5,6,7-tetrahydro-imidazo-[4,5-c]-pyridine and 7.47 g of cyclopropyl isocyanate in 20 ml of dry dioxane is refluxed for 1.5 h. After evaporation to dryness, the residue is dissolved in 44 ml of methanol and treated with 11 ml of 2N sodium hydroxide for 1.5 h at room temperature. After neutralization, the solution is extracted with chloroform. Evaporation of the solvent leaves a residue that is taken up in acetonitrile to give 2.12 g of the title compound, m.p. 215°.

EXAMPLE 33

5-(N-cyclopentyl-carbamoyl)-4,5,6,7-tetrahydro-imidazo-[4,5-c]-pyridine (386/1366)

Operating as in Example 32, but employing cyclopentyl isocyanate, 3.46 g of the title compound, m.p. 225°, are obtained.

EXAMPLE 34

5-(N-cyclopentyl-thiocarbamoyl)-b 4,5,6,7-tetrahydro-imidazo-[4,5-c]-pyridine (386/1360)

Operating as in Example 2, but employing cyclopentyl isothiocyanate, the title compound, m.p. 185°, is obtained in 60% yield.

EXAMPLE 35

5-(N-cyclopropyl-thiocarbamoyl)-4,5,6,7-tetrahydro-imidazo-[4,5-c]-pyridine (386/1359)

A solution of 2.462 g of 4,5,6,7-tetrahydro-imidazo-[4,5-c]-pyridine and 2.97 g of cyclopropyl isothiocyanate in 20 ml of acetonitrile is refluxed for 7 h. After evaporation to dryness, the residue is chromatographed on silica gel (ethyl acetate ethanol as eluant) to give 1.42 g of the pure title compound, m.p. 185°.

EXAMPLE 36

4-Cyclohexyl-5-(N-methyl-thiocarbamoyl)-4,5,6,7-tetrahydro-imidazo-[4,5-c]-pyridine (386/1368)

Operating as in Example 14, 15.5 g of 4-cyclohexyl-4,5,6,7-tetrahydro-imidazo-[4,5-c]-pyridine, m.p. 150°, are obtained from 18.4 g of histamine dihydrochloride and 24.4 ml of hexahydrobenzaldehyde. A solution of 2.05 g of 4-cyclohexyl-4,5,6,7-tetrahydro-imidazo-[4,5-c]-pyridine and 1.1 g of methyl isothiocyanate in 30 ml of acetonitrile is refluxed for 5 h. The solution is cooled and filtered, and 2.50 g of the title compound, m.p. 232°, are collected.

EXAMPLE 37

4-Cyclohexyl-5-(N-isopropyl-thiocarbamoyl)-4,5,6,7-tetrahydro-imidazo-[4,5-c]-pyridine (386/1367)

Operating as in Example 36, 2.53 g of the title compound, m.p. 218° are obtained from 2.05 g of 4-cyclohexyl-4,5,6,7-tetrahydro-imidazo-[4,5-c]-pyridine and 1.52 g of isopropyl isothiocyanate.

EXAMPLE 38

4-(2-thienyl)-5-N-isopropyl-thiocarbamoyl)-4,5,6,7-tetrahydro-imidazo-[4,5-c]-pyridine (386/1369)

Operating as in Example 14, 15 g of 4-(2-thienyl)-4,5,6,7-tetrahydro-imidazo-[4,5-c]-pyridine, m.p. 170°, are obtained from 18.4 g of histamine dihydrochloride and 18.4 ml of 2-thiophenaldehyde. A solution of 2.05 g of 4-(2-thienyl)-4,5,6,7-tetrahydro-imidazo-[4,5-c]-pyridine and 1.52 g of isopropyl isothiocyanate in 30 ml of acetonitrile is refluxed for 5 h. The solution is cooled and filtered: 2.18 g of the title compound, m.p. 205°, are collected.

EXAMPLE 39

4-(2-thienyl)-5-(N-methyl-thiocarbamoyl)-4,5,6,7-tetrahydro-imidazo-[4,5-c]-pyridine (386/1383)

Operating as in Example 38, the title compound is obtained in 66% yield, m.p. 215°.

EXAMPLE 40

4-(2-furyl)-5-(N-methyl-thiocarbamoyl)-4,5,6,7-tetrahydro-imidazo-[4,5-c]-pyridine (386/1372)

Operating as in Example 14, 12 g of 4-(2-furyl)-4,5,6,7-tetrahydro-imidazo-[4,5-c]-pyridine (oil) are obtained from 18.4 g of histamine dihydrochloride and 16.6 ml of furfural. A solution of 1.89 g of 4-(2-furyl)-4,5,6,7-tetrahydro-imidazo-[4,5-c]-pyridine and 1.1 g of methyl isothiocyanate in 20 ml of acetonitrile is refluxed for 5 h. The solution is cooled and filtered: 1.54 g of the title compound, m.p. 200°, are collected.

EXAMPLE 41

4-(2-furyl)-5-(N-isopropyl)-thiocarbamoyl)-4,5,6,7-tetrahydro-imidazo-[4,5-c]-pyridine (386/1373)

Operating as in Example 40, 1.61 g of the title compound, m.p. 195°, are obtained from 1.89 g of 4-(2-furyl)-4,5,6,7-tetrahydro-imidazo-[4,5-c]-pyridine and 1.52 g of isopropyl isothiocyanate.

EXAMPLE 42

4-Cyclohexyl-5-(N-methyl-carbamoyl)-4,5,6,7-tetrahydro-imidazo-[4,5-c]-pyridine (386/1374)

Operating as in Example 28, 3.1 g of the title compound, m.p. 250°, are obtained from 4.1 g of 4-cyclohexyl-4,5,6,7-tetrahydro-imidazo-[4,5-c]-pyridine.

EXAMPLE 43

4-Cyclohexyl-5-(N-isopropyl-carbamoyl)-4,5,6,7-tetrahydro-imidazo-[4,5-c]-pyridine (386/1375)

Operating as in Example 29, 3.45 g of the title compound, crystallized from ethanol and melting at 254°, are obtained from 4.1 g of 4-cyclohexyl-4,5,6,7-tetrahydro-imidazo-[4,5-c]-pyridine.

EXAMPLE 44

4-(2-thienyl)-5-(N-isopropyl-carbamoyl)-4,5,6,7-tetrahydro-imidazo-[4,5-c]-pyridine (386/1376)

Operating as in Example 26, but employing isopropyl isocyanate, 2.3 g of the title compound, crystallized from ethanol and melting at 223° (dec.), are obtained from 3.5 g of 4-(2-thienyl-4,5,6,7-tetrahydro-imidazo-[4,5-c]-pyridine.

EXAMPLE 45

4-Isopropyl-5-(N-isopropyl-carbamoyl)-4,5,6,7-tetrahydro-imidazo-[4,5-c]-pyridine (386/1377)

Operating as in Example 26, but employing isopropyl isocyanate, 2.8 g of the title compound, crystallized from acetonitrile and melting at 202°, are obtained from 2.48 g of 4-isopropyl-4,5,6,7-tetrahydro-imidazo-[4,5-c]-pyridine.

EXAMPLE 46

4-(2-thienyl)-5-(N-methyl-carbamoyl)-4,5,6,7-tetrahydro-imidazo-[4,5-c]-pyridine (386/1378)

Operating as in Example 26, 1.14 g of the title compound, crystallized from acetonitrile and melting at 230°, are obtained from 3.5 g of 4-(2-thienyl)-4,5,6,7-tetrahydro-imidazo-[4,5-c]-pyridine.

EXAMPLE 47

4-(2-furyl)-5-(N-methyl-carbamoyl)-4,5,6,7-tetrahydro-imidazo-[4,5-c]-pyridine (386/1379)

Operating as in Example 26, 1.55 g of the title compound, crystallized from acetonitrile and melting at 205°, are obtained from 1.89 g of 4-(2-furyl)-4,5,6,7-tetrahydro-imidazo-[4,5-c]-pyridine.

EXAMPLE 48

4-(2-furyl)-5-(N-isopropyl-carbamoyl)-4,5,6,7-tetrahydro-imidazo-[4,5-c]-pyridine (386/1382)

Operating as in Example 26, but employing isopropyl isocyanate, 2.23 g of the title compound, crystallized from acetonitrile and melting at 237° (dec.), are obtained from 2.84 g of 4-(2-furyl)-4,5,6,7-tetrahydro-imidazo-[4,5-c]-pyridine.

EXAMPLE 49

3-Methyl-4-ethyl-5-(N-isopropyl-thiocarbamoyl)-4,5,6,7-tetrahydro-imidazo-[4,5-c]-pyridine (386/1391)

Operating as in Example 17, the title compound crystallized from ethanol and melting at 196°, is obtained in 50% yield.

EXAMPLE 50

4-Phenyl-5-guanyl-4,5,6,7-tetrahydro-imidazo-[4,5-c]-pyridine (386/1401)

Operating as in Example 20, the monohydrochloride of the title compound, crystallized from ethanol and melting at 288° (dec.), is obtained in 80% yield.

EXAMPLE 51

4-Cyclohexyl-5-guanyl-4,5,6,7-tetrahydro-imidazo-[4,5-c]-pyridine (386/1405)

Operating as in Example 20, the monohydrochloride of the title compound, crystallized from ethanol and melting at 305° (dec.), is obtained in 60% yield.

EXAMPLE 52

3,4-Diethyl-5-(N-isopropyl-thiocarbamoyl)-4,5,6,7-tetrahydroimidazo-[4,5-c]-pyridine (386/1399)

A solution of 9.3 g of 3,4-diethyl-4,5,6,7-tetrahydro-imidazo-[4,5-c]-pyridine and 7.59 g of isopropyl isothiocyanate in 75 ml of anhydrous CH$_3$CN is refluxed for 7.5 hours. The solution is allowed to stand overnight at −15° C., then is filtered. 5.59 g of the crude title compound are collected; m.p. 195° C. (recrystallized from CH$_3$CN).

EXAMPLE 53

4-(4-pyridyl)-5-(N-methylthiocarbamoyl)-4,5,6,7-tetrahydroimidazo-[4,5-c]-pyridine (386/1454)

Operating as described in Example 14, but employing 4-pyridine-carboxyaldehyde, from 18.4 g of histamine dihydrochloride 25 g of 4-(4-pyridyl)-4,5,6,7-tetrahydroimidazo-[4,5-c]-pyridine are obtained. The free base is obtained by treatment with Amberlite IRA 410 ion-exchange resin.

A solution of 1.5 g of the free base and 876 mgr of methyl isothiocyanate in 25 ml of anhydrous CH$_3$CN is refluxed for 7 hours. The solution is cooled and filtered;

0.9 g of the title compound are collected (m.p. 160° C., from CH₃CN).

EXAMPLE 54

4-(3-pyridyl)-5-(N-methylthiocarbamoyl)-4,5,6,7-tetrahydroimidazo-[4,5-c]-pyridine (386/1455)

Operating as described in Example 14, but employing 3-pyridine-carboxyaldehyde from 18.4 g of histamine dihydrochloride, 24 g of 4-(3-pyridyl)-4,5,6,7-tetrahydroimidazo-[4,5-c]-pyridine trihydrochlorie are obtained.

The free base is obtained by treatment with Amberlite IRA 410-ion-exchange resin.

Operating as in the previous Example, from 1.5 g of the base 1.5 g of the title compound (m.p. 240° C. from EtOH) are obtained.

EXAMPLE 55

3-Methyl-4-ethyl-5-(N-isopropyl-carbamoyl)-4,5,6,7-tetrahydroimidazo-[4,5-c]-pyridine (386/1404)

Operating as described in Example 26, from 2 g of 3-methyl-4-ethyl-4,5,6,7-tetrahydroimidazo-[4,5-c]-pyridine, 1.2 g of the title compound (m.p. 220° C. from CH₃CN) are obtained.

EXAMPLE 56

3,4-Diethyl-5-(N-isopropyl-carbamoyl)-4,5,6,7-tetrahydro-imidazo-[4,5-c]-pyridine (386/1400)

Operating as described in Example 26, from 4 g of 3,4-diethyl-4,5,6,7-tetrahydroimidazo-[4,5-c]-pyridine, 2.5 g of the title compound (m.p. 155° C. from CH₃CN) are obtained.

EXAMPLE 57

4-(4-pyridyl)-5-(N-isopropyl-carbamoyl)-4,5,6,7-tetrahydroimidazo-[4,5-c]-pyridine (386/1467)

Operating as described in Example 26, from 2 g of 4-(4-pyridyl)-4,5,6,7-tetrahydroimidazo-[4,5-c]-pyridine, 1.8 g of the title compound (m.p. 212° C. from CH₃CN) are obtained.

EXAMPLE 58

4-(3-pyridyl)-5-(N-isopropyl-carbamoyl)-4,5,6,7-tetrahydroimidazo-[4,5-c]-pyridine (386/1457)

Operating as described in Example 26, from 2 g of 4-(3-pyridyl)-4,5,6,7-tetrahydroimidazo-[4,5-c]-pyridine, 1.4 g of the title compound (m.p. 237° C. from CH₃CN) are obtained.

EXAMPLE 59

4-(2-pyridyl)-5-(N-isopropyl-carbamoyl)-4,5,6,7-tetrahydroimidazo-[4,5-c]-pyridine (386/1482)

Operating as described in Example 14, but employing 2-pyridine-carboxyaldehyde, from 18.4 g of histamine dihydrochloride 23 g of 4-(2-pyridyl)-4,5,6,7-tetrahydroimidazo-[4,5-c]-pyridine trihydrochloride are obtained. The free base is obtained by exchange on Amberlite ion-exchange resin IRA 410.

Operating as in Example 26, from 2 g of the base, 1.5 g of the title compound (m.p. 240° C. from CH₃CN) are obtained.

EXAMPLE 60

4-Ethyl-5-(N-benzoylguanyl)-4,5,6,7-tetrahydroimidazo-[4,5-c]-pyridine (386/1448)

A solution of 1.51 g of 4-ethyl-4,5,6,7-tetrahydroimidazo-[4,5-c]-pyridine and 2.92 g of Ph—CO—N-H—CN (benzoylcyanamide) in 20 ml of anhydrous ethanol is refluxed for 8 hours.

After addition of 2.92 g of benzoylcyanamide, the solution is refluxed again for 8 hours.

After evaporation to dryness, two equivalents of aqueous hydrogen chloride are added.

After evaporation to dryness, the residue is taken up in water and filtered off. The filtrate is washed with CHCl₃, and the aqueous layer is evaporated to dryness. The residue is crystallized from EtOH and 3.3 g of the dihydrochloride of the title compound (m.p. 210° C.) are obtained.

EXAMPLE 61

5-(N-benzoylguanyl)-4,5,6,7-tetrahydroimidazo-[4,5-c]-pyridine (386/1450)

Operating as described in the previous Example, from 1.23 g of 4,5,6,7-tetrahydroimidazo-[4,5-c]-pyridine, 3 g of the dihydrochloride of the title compound (m.p. 228° C. from isopropanol) are obtained.

For the convenience of those concerned, Table II below gives the identification of the various substituents in formula I for the compounds of the working examples:

TABLE II

| Example No. | R₁ | R₂ | R₃ | R₄ | X |
|---|---|---|---|---|---|
| 1 | H | H | CH₃ | | S |
| 2 | H | H | C₂H₅ | | S |
| 3 | H | H | C₃H₇ | | S |
| 4 | H | H | i-C₃H₇ | | S |
| 5 | H | H | n-C₄H₉ | | S |
| 6 | H | H | cyclohexyl | | S |
| 7 | H | C₂H₅ | CH₃ | | S |
| 8 | H | H | allyl | | S |
| 9 | H | C₂H₅ | i-C₃H₇ | | S |
| 10 | H | C₂H₅ | allyl | | S |
| 11 | H | C₂H₅ | n-C₄H₉ | | S |
| 12 | H | phenyl | CH₃ | | S |
| 13 | H | phenyl | i-C₃H₇ | | S |
| 14 | H | i-C₃H₇ | CH₃ | | S |
| 15 | H | i-C₃H₇ | i-C₃H₇ | | S |
| 16 | CH₃ | H | CH₃ | | S |
| 17 | CH₃ | H | i-C₃H₇ | | S |
| 18 | H | H | phenyl | | S |
| 19 | H | H | CH₃ | CN | NR₄ |
| 20 | H | H | H | H | NR₄ |
| 21 | H | C₂H₅ | H | H | NR₄ |
| 22 | H | C₂H₅ | C₂H₅ | H | NR₄ |
| 23 | H | C₂H₅ | i-C₃H₇ | H | NR₄ |
| 24 | H | H | C₂H₅ | H | NR₄ |
| 25 | H | H | i-C₃H₇ | H | NR₄ |
| 26 | H | phenyl | CH₃ | | O |
| 27 | H | phenyl | i-C₃H₇ | | O |
| 28 | H | C₂H₅ | CH₃ | | O |
| 29 | H | C₂H₅ | i-C₃H₇ | | O |
| 30 | H | H | CH₃ | | O |
| 31 | H | H | i-C₃H₇ | | O |
| 32 | H | H | cyclopropyl | | O |
| 33 | H | H | cyclopentyl | | O |
| 34 | H | H | cyclopentyl | | S |
| 35 | H | H | cyclopropyl | | S |
| 36 | H | cyclohexyl | CH₃ | | S |
| 37 | H | cyclohexyl | i-C₃H₇ | | S |
| 38 | H | thienyl | i-C₃H₇ | | S |
| 39 | H | thienyl | CH₃ | | S |
| 40 | H | furyl | CH₃ | | S |
| 41 | H | furyl | i-C₃H₇ | | S |
| 42 | H | cyclohexyl | CH₃ | | O |
| 43 | H | cyclohexyl | i-C₃H₇ | | O |
| 44 | H | thienyl | i-C₃H₇ | | O |
| 45 | H | i-C₃H₇ | i-C₃H₇ | | O |
| 46 | H | thienyl | CH₃ | | O |
| 47 | H | furyl | CH₃ | | O |

TABLE II-continued

| Example No. | R₁ | R₂ | R₃ | R₄ | X |
|---|---|---|---|---|---|
| 48 | H | furyl | i-C₃H₇ | | O |
| 49 | CH₃ | C₂H₅ | i-C₃H₇ | | S |
| 50 | H | phenyl | H | H | NR₄ |
| 51 | H | cyclohexyl | H | H | NR₄ |
| 52 | C₂H₅ | C₂H₅ | i-C₃H₇ | | S |
| 53 | H | 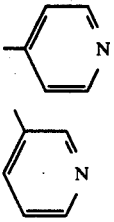 | CH₃ | | S |
| 54 | H | 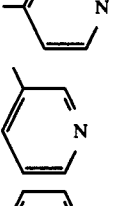 | CH₃ | | S |
| 55 | CH₃ | C₂H₅ | i-C₃H₇ | | O |
| 56 | C₂H₅ | C₂H₅ | i-C₃H₇ | | O |
| 57 | H | 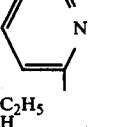 | i-C₃H₇ | | O |
| 58 | H | 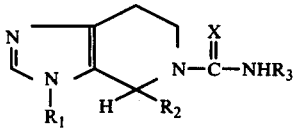 | i-C₃H₇ | | O |
| 59 | H |  | i-C₃H₇ | | O |
| 60 | H | C₂H₅ | C₆H₅—CO— | H | NR₄ |
| 61 | H | H | C₆H₅—CO— | H | NR₄ |

What is claimed is:

1. A compound of the formula I:

I where
R₁ is hydrogen or an alkyl having from 1 to 4 carbon atoms;
R₂ is hydrogen, an alkyl having from 1 to 4 carbon atoms, a cycloalkyl having from 3 to 6 carbon atoms or phenyl;
R₃ is hydrogen, a saturated or unsaturated straight or branched alkyl having from 1 to 6 carbon atoms, a cycloalkyl having from 3 to 6 carbon atoms, benzoyl or phenyl; and
X is O or S;
or a pharmaceutically acceptable acid addition salt thereof.

2. A compound as defined in claim 1, which is 5-(N-methyl-thiocarbamoyl)-4,5,6,7-tetrahydroimidazo-[4,5,-c]-pyridine.

3. A compound as defined in claim 1, which is 5-(N-ethyl-thiocarbamoyl)-4,5,6,7-tetrahydroimidazo-[4,5-c]-pyridine.

4. A compound as defined in claim 1, which is 5-(N-n-propyl-thiocarbamoyl)-4,5,6,7-tetrahydroimidazo-[4,5-c]-pyridine.

5. A compound as defined in claim 1, which is 5-(N-isopropyl-thiocarbamoyl)-4,5,6,7-tetrahydroimidazo-[4,5-c]-pyridine.

6. A compound as defined in claim 1, which is 5-(N-n-butyl-thiocarbamoyl)-4,5,6,7-tetrahydroimidazo-[4,5-c]-pyridine.

7. A compound as defined in claim 1, which is 5-(N-cyclohexyl-thiocarbamoyl)-4,5,6,7-tetrahydroimidazo-[4,5-c]-pyridine.

8. A compound as defined in claim 1, which is 4-Ethyl-5-(N-methyl-thiocarbamoyl)-4,5,6,7-tetrahydro-imidazo-[4,5-c]-pyridine.

9. A compound as defined in claim 1, which is 5-(N-allyl-thiocarbamoyl)-4,5,6,7-tetrahydroimidazo-[4,5-c]-pyridine.

10. A compound as defined in claim 1, which is 4-Ethyl-5-(N-isopropyl-thiocarbamoyl)-4,5,6,7-tetrahydroimidazo-[4,5-c]-pyridine.

11. A compound as defined in claim 1, which is 4-Ethyl-5-(N-allyl-thiocarbamoyl)-4,5,6,7-tetrahydroimidazo-[4,5-c]-pyridine.

12. A compound as defined in claim 1, which is 4-Ethyl-5-(N-butyl-thiocarbamoyl)-4,5,6,7-tetrahydroimidazo-[4,5-c]-pyridine.

13. A compound as defined in claim 1, which is 4-Phenyl-5-(N-methyl-thiocarbamoyl)-4,5,6,7-tetrahydroimidazo-[4,5-c]-pyridine.

14. A compound as defined in claim 1, which is 4-Phenyl-5-(N-isopropyl-thiocarbamoyl)-4,5,6,7-tetrahydroimidazo-[4,5-c]-pyridine.

15. A compound as defined in claim 1, which is 4-Isopropyl-5-(N-methyl-thiocarbamoyl)-4,5,6,7-tetrahydroimidazo-[4,5-c]-pyridine.

16. A compound as defined in claim 1, which is 4-Isopropyl-5-(N-isopropyl-thiocarbamoyl)-4,5,6,7-tetrahydroimidazo-[4,5-c]-pyridine.

17. A compound as defined in claim 1, which is 3-Methyl-5-(N-methyl-thiocarbamoyl)-4,5,6,7-tetrahydroimidazo-[4,5-c]-pyridine.

18. A compound as defined in claim 1, which is 3-Methyl-5-(N-isopropyl-thiocarbamoyl)-4,5,6,7-tetrahydroimidazo-[4,5-c]-pyridine.

19. A compound as defined in claim 1, which is 5-(N-Phenyl-thiocarbamoyl)-4,5,6,7-tetrahydroimidazo-[4,5-c]-pyridine.

20. A compound as defined in claim 1, which is 4-Phenyl-5-(N-methyl-carbamoyl)-4,5,6,7-tetrahydroimidazo-[4,5-c]-pyridine.

21. A compound as defined in claim 1, which is 4-Phenyl-5-(N-isopropyl-carbamoyl)-4,5,6,7-tetrahydroimidazo-[4,5-c]-pyridine.

22. A compound as defined in claim 1, which is 4-Ethyl-5-(N-methyl-carbamoyl)-4,5,6,7-tetrahydroimidazo-[4,5-c]-pyridine.

23. A compound as defined in claim 1, which is 4-Ethyl-5-(N-isopropyl-carbamoyl)-4,5,6,7-tetrahydroimidazo-[4,5-c]-pyridine.

24. A compound as defined in claim 1, which is 5-(N-methyl-carbamoyl)-4,5,6,7-tetrahydroimidazo-[4,5-c]-pyridine.

25. A compound as defined in claim 1, which is 5-(N-isopropyl-carbamoyl)-4,5,6,7-tetrahydroimidazo-[4,5-c]-pyridine.

26. A compound as defined in claim 1, which is 5-(N-cyclopropyl-carbamoyl)-4,5,6,7-tetrahydroimidazo-[4,5-c]-pyridine.

27. A compound as defined in claim 1, which is 5-(N-cyclopentyl-carbamoyl)-4,5,6,7-tetrahydroimidazo-[4,5-c]-pyridine.

28. A compound as defined in claim 1, which is 5-(N-cyclopentyl-thiocarbamoyl)-4,5,6,7-tetrahydroimidazo-[4,5-c]-pyridine.

29. A compound as defined in claim 1, which is 5-(N-cyclopropyl-thiocarbamoyl)-4,5,6,7-tetrahydroimidazo-[4,5-c]-pyridine.

30. A compound as defined in claim 1, which is 4-Cyclohexyl-5-(N-methyl-thiocarbamoyl)-4,5,6,7-tetrahydroimidazo-[4,5-c]-pyridine.

31. A compound as defined in claim 1, which is 4-Cyclohexyl-5-(N-isopropyl-thiocarbamoyl)-4,5,6,7-tetrahydroimidaco-[4,5-c]-pyridine.

32. A compound as defined in claim 1, which is 4-Cyclohexyl-5-(N-methyl-carbamoyl)-4,5,6,7-tetrahydroimidazo-[4,5-c]-pyridine.

33. A compound as defined in claim 1, which is 4-Cyclohexyl-5-(N-isopropyl-carbamoyl)-4,5,6,7-tetrahydroimidazo-[4,5-c]-pyridine.

34. A compound as defined in claim 1, which is 4-Isopropyl-5-(N-isopropyl-carbamoyl)-4,5,6,7-tetrahydroimidazo-[4,5-c]-pyridine.

35. A compound as defined in claim 1, which is 3-Methyl-4-ethyl-5-(N-isopropyl-thiocarbamoyl)-4,5,6,7-tetrahydroimidazo-[4,5-c]-pyridine.

36. A compound as defined in claim 1, which is 3,4-Diethyl-5-(N-isopropyl-thiocarbamoyl)-4,5,6,7-tetrahydroimidazo-[4,5-c]-pyridine.

37. A compound as defined in claim 1, which is 3-Methyl-4-ethyl-5-(N-isopropyl-carbamoyl)-4,5,6,7-tetrahydroimidazo-[4,5-c]-pyridine.

38. A compound as defined in claim 1, which is 3,4-Diethyl-5-(N-isopropyl-carbamoyl)-4,5,6,7-tetrahydroimidazo-[4,5-c]-pyridine.

* * * * *

UNITED STATES PATENT AND TRADEMARK OFFICE
CERTIFICATE OF CORRECTION

PATENT NO. : 4,141,899

DATED : February 27, 1979

INVENTOR(S) : Giuliana ARCARI et al

It is certified that error appears in the above-identified patent and that said Letters Patent are hereby corrected as shown below:

Column 1, line 58, change "(100-200 g)" to --(100-120 g)--;

Column 2, in the Table, the values corresponding to compound No. 1399 should be indicated in the following order:
--1399    3.5    4    10    >100    >25--

Column 4, Example 7, "4-Ethyl-5-(N-methyl-thiocarbamoyl)-4,5,6,6..." should read --4-Ethyl-5-(N-methyl-thiocarbamoyl)-4,5,6,7...--

Column 11, Example 54, line 11, "trihydrochlorie" should read --trihydrochloride--.

Signed and Sealed this

Seventh Day of August 1979

[SEAL]

Attest:

LUTRELLE F. PARKER

*Attesting Officer*    *Acting Commissioner of Patents and Trademarks*